United States Patent
Ephraim et al.

(10) Patent No.: US 11,439,616 B2
(45) Date of Patent: Sep. 13, 2022

(54) COMPOSITIONS AND METHODS OF TREATING AND REDUCING RISK OF CONDITIONS ASSOCIATED WITH ELEVATED 4-ETHYLPHENYL SULFATE

(71) Applicant: Hill's Pet Nutrition, Inc., Topeka, KS (US)

(72) Inventors: Eden Ephraim, Lawrence, KS (US); Dennis Jewell, Lawrence, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 196 days.

(21) Appl. No.: 16/721,466

(22) Filed: Dec. 19, 2019

(65) Prior Publication Data

US 2021/0186912 A1    Jun. 24, 2021

(51) Int. Cl.

| | | |
|---|---|---|
| *A61K 31/202* | (2006.01) | |
| *A61K 31/375* | (2006.01) | |
| *A61P 25/22* | (2006.01) | |
| *A61K 47/46* | (2006.01) | |
| *A61K 9/00* | (2006.01) | |
| *A61K 31/355* | (2006.01) | |

(52) U.S. Cl.
CPC .......... *A61K 31/202* (2013.01); *A61K 9/0056* (2013.01); *A61K 31/355* (2013.01); *A61K 31/375* (2013.01); *A61K 47/46* (2013.01); *A61P 25/22* (2018.01)

(58) Field of Classification Search
CPC .................................................. A61K 31/202
See application file for complete search history.

(56) References Cited

FOREIGN PATENT DOCUMENTS

WO    2020/131007 A1    6/2020

OTHER PUBLICATIONS

Hall JA and Jewell DE. Feeding healthy beagles medium-chain triglycerides, fish oil, and carnitine offsets age-related changes in serum fatty acids and carnitine metabolites. Plos One 7 (2012): e49510.*

Dzanis, Fatty acids: AAFCO Dog and Cat Food Nutrient Profiles, May 11, 2016, available at https://www.petfoodindustry.com/articles/5807-fatty-acids-aafco-dog-and-cat-food-nutrient-profiles?v=preview.*
Pusceddu et al., N-3 Polyunsaturated Fatty Acids (PUFAs) Reverse the Impact of Early-Life Stress on the Gut Microbiota, PLoS One Oct. 1, 2015;10(10):e0139721.*
Buddington et al., Influence of fermentable fiber on small intestinal dimensions and transport of glucose and proline in dogs. American Journal of Veterinary Research 60 (1999): 354-358 (Abstract).*
Dorrestein, From microbiomess to metabolomes to function during host-microbial interactions, Immunity. Jun. 19, 2014; 40(6): 824-832.*
Burokas et al., 2015, "Targeting the microbiota-gut brain axis for stress-related disorders: prebiotics selectively Yeduce anxiety in mice", European Neuropsychopharmacology, 25(1):S44-S45.
International Search Report and the Written Opinion of the International Searching Authority issued in International Application PCT/US2019/067568 dated Sep. 17, 2020.
Martin et al., 2018, "Gut Microbiota and Dietary Fiber Mitigate Amino Acid Stress Response in Low-Protein Diets", Current Developments in Nutrition, Cedars-Sinai Mexical Center, 2(11):nzy037.
Marzorati et al., 2017, "High-fiber and high-protein diets shape different gut microbial communities, which ecologically behave similarly under stress conditions, as shown in a gastrointestinal simulator", Molecular Nutrition & Food Research, 61(1), (13 pages).
Pusceddu et al., 2015, "N-3 Polyunsaturated Fatty Acids (PUFAs) Reverse the Impact of Early-Life Stress on the Gut Microbiota", PLoS ONE, e0139721-e0139721, (13 pages).
Rabot et al., 2018, "Links between the Gut Microbiota and Anxiety- and Depression-like Behavior in Rodents", Phytotherapie, 16(6):306-314.
Soares et al., 2019, "In Vitro Exploration of Healthy and Stressed Gut Microbiota Metabolism", Current Developments in Nutrition, Oxford University Press,3(1):1760.

* cited by examiner

*Primary Examiner* — Svetlana M Ivanova (57) ABSTRACT

Compositions and methods of treating anxiety or stress in an animal are disclosed. Compositions and methods of reducing or preventing elevated levels of 4-EPS are disclosed. Compositions and methods for promoting growth of beneficial microbes in an animal's microbiome and inhibiting growth of non-beneficial microbes are disclosed. The methods comprise administering to the animal an effective amount of n-3 fatty acids, antioxidants, insoluble fiber and soluble fiber in an effective ratio of insoluble fiber and soluble fiber. Compositions comprise effective amounts of n-3 fatty acids, antioxidants, insoluble fiber and soluble fiber in an effective ratio of insoluble fiber and soluble fiber.

29 Claims, 1 Drawing Sheet

COMPOSITIONS AND METHODS OF TREATING AND REDUCING RISK OF CONDITIONS ASSOCIATED WITH ELEVATED 4-ETHYLPHENYL SULFATE

BACKGROUND

The microbial toxin, 4-ethylphenyl sulfate (4-EPS) is a metabolite produced by gut microbes. Among other microbial metabolites, 4-EPS enters the systemic circulation. Increased levels of 4-EPS in the blood, particularly in canines, is associated with stress, anxiety, brain damage and other behavioral issues. Reduction in levels of 4-EPS has been shown to alleviate symptoms of stress and anxiety.

Canine anxiety (anxiety) is a response to fear and agitation, or apprehension when the dog anticipates a threat or fearful situation. Some individual dogs experience disproportionate levels of anxiety. Anxiety can develop into an anxiety disorder and can lead to behavioral and other issues. Some dogs experience a generalized anxiety, in which the fearful reaction is displayed in a wide range of situations to which a "normal" pet would be unlikely to react. Anxiety can take the form of one of various anxiety disorders such as generalized anxiety disorders, excessive stimulus anxiety, separation anxiety, confinement, noise phobias, among others.

Causative factors may include genetic components, prenatal and neonatal stressors, maternal separation, lack of socialization, unfamiliarity, or a previous unpleasant outcome during encounters with the stimulus (or similar stimuli). The most common causes are fear, separation and aging. Fear-related anxiety can be caused by loud noises, strange people or animals, visual stimuli, new or strange environments, and specific situations among others. Age-related anxiety affects older dogs and can be associated with cognitive dysfunction syndrome (CDS). Separation anxiety is a specific anxiety arising from an inability of the pet to find comfort when separated from family members. About 14% of dogs have separation anxiety. Some separation anxiety may be the result of dysfunctional attachment as a puppy ages and matures. In some cases, separation anxiety may arise in cases involving a change in household or daily routine, while in others separation anxiety is associated with an underlying state of anxiety along with other behavioral issues such as phobias.

Anxiety may lead to destructive behavior (particularly at exits or toward owner possessions), distress vocalization, house-soiling, salivation, pacing, restlessness, inability to settle, anorexia, and repetitive or compulsive behaviors. In some instances, anxiety may play a role in aggressive behavior.

Common symptoms of dog anxiety include aggression, urinating or defecating in the house, drooling, panting, destructive behavior, depression, excessive barking, pacing, restlessness and repetitive or compulsive behaviors. Different dogs display different symptoms and combinations of symptoms when suffering from anxiety.

Canine stress is the response of dog to a demand placed upon it to change or adapt, typically exhibited as feelings of strain or pressure. Canine stress may cause in feelings of fear, agitation, hyperactivity, nervousness, oversensitivity or irritability. Negative stress, excessive stress and chronic stress can have a detrimental effect on behavior, health and overall well-being. Stress has the potential to bring on illness, suppress the immune system, cause undesirable behaviors, and increase arousal, which increases the probability of aggressive behavior.

Causes of stress in dogs include grief, exposure to conflict, excessive or insufficient stimulation, overcrowded conditions, environmental changes (schedule, people, animals, increased noise); punitive training, insufficient social time, frightening events, neglect, frustration, and uncertainty among others.

Dogs communicate that they are experiencing stress in different ways. Some indications that a dog is experiencing stress include dilated pupils, tightness around eyes, whale eye/half-moon eyes, yawning, lip/nose licking, panting, excess salivation, smiling, teeth chattering, cheek puffing, showing teeth, wrinkled muzzle, pinned back or upright ears. Other indications include tense body, stretching, excessive shedding, little or no movement, low body posture, weight shifted back, trembling/shaking, penis crowning, sweaty paws, tight brow, barking, growling, howling and whining. When stressed, a dog's behavior will often change. Common behaviors that are often stress induced include restlessness, insufficient or excessive sleeping, jumpiness/hypervigilance, irritability, excessive self-grooming, destructive behavior, loss of appetite, obsessive/compulsive behaviors, inability to focus, hyperactivity, increased urination and defecation, and vomiting and diarrhea among others.

There is a need for methods and compositions for reducing elevated levels of 4-EPS in canines. There is a need for methods and compositions for treating or reducing the severity of elevated levels of canine anxiety. There is a need for methods and compositions for treating or reducing the severity of elevated levels of canine stress.

BRIEF SUMMARY

Methods for treating anxiety or stress in an animal are provided. The methods comprise administering to the animal effective amounts of n-3 fatty acids, antioxidants, insoluble fiber and soluble fiber in an effective ratio of insoluble fiber and soluble fiber.

Methods for reducing elevated levels of 4-EPS in an animal with elevated 4-EPS levels are provided. The methods comprise administering to the animal effective amounts of n-3 fatty acids, antioxidants, insoluble fiber and soluble fiber in an effective ratio of insoluble fiber and soluble fiber.

Methods for preventing elevated levels of 4-EPS in an animal are provided. The methods comprise administering to the animal at risk of elevated 4-EPS levels effective amounts of n-3 fatty acids, antioxidants, insoluble fiber and soluble fiber in an effective ratio of insoluble fiber and soluble fiber.

Methods for promoting growth of beneficial microbes in an animal's microbiome and inhibiting growth of non-beneficial microbes are provided. The methods comprise administering to the animal effective amounts of n-3 fatty acids, antioxidants, insoluble fiber and soluble fiber in an effective ratio of insoluble fiber and soluble fiber.

Compositions for treating anxiety or stress in an animal are provided. The compositions comprise effective amounts of n-3 fatty acids, antioxidants, insoluble fiber and soluble fiber in an effective ratio of insoluble fiber and soluble fiber.

Compositions for reducing elevated levels of 4-EPS in an animal with elevated 4-EPS levels are provided. The compositions comprise effective amounts of n-3 fatty acids, antioxidants, insoluble fiber and soluble fiber in an effective ratio of insoluble fiber and soluble fiber.

Compositions for preventing elevated levels of 4-EPS in an animal are provided. The compositions comprise effective amounts of n-3 fatty acids, antioxidants, insoluble fiber and soluble fiber in an effective ratio of insoluble fiber and soluble fiber.

Compositions for promoting growth of beneficial microbes in an animal's microbiome and inhibiting growth of non-beneficial microbes are provided. The compositions comprise effective amounts of n-3 fatty acids, antioxidants, insoluble fiber and soluble fiber in an effective ratio of insoluble fiber and soluble fiber.

DETAILED DESCRIPTION

The following description of the preferred embodiment(s) is merely exemplary in nature and is in no way intended to limit the invention, its application, or uses.

As used herein and in the appended claims, the singular forms "a", "an", and "the" include plural reference unless the context clearly dictates otherwise.

As used herein, the term "companion animal" includes any non-human animal suitable for being kept as a pet by humans including without limitation, a dog, a cat, rabbit and a rodent. Some specific embodiments are formulations and methods of treatment for dogs and/or cats. In one specific aspect, formulations and methods of treatment for dogs are provided.

The term "dog" includes those dogs which are companion animals such as *Canis familiaris*, working dogs and the like. The term dog is synonymous with the term canine.

The term "cat" includes those cats which are companion animals known as domestic cats or house cats, or *Felis domesticus*. The term cat is synonymous with the term feline.

The terms "high solubility fiber" and "soluble fiber" may be used interchangeably.

The terms "low solubility fiber" and "insoluble fiber" may be used interchangeably.

The terms n-3 fatty acids and omega-3-fatty acids may be used interchangeably.

Methods are provided for treating anxiety and stress in an animal, particularly a companion animal such as a canine or feline. The methods comprise administering to the animal a combination of effective amounts of n-3 fatty acids, antioxidants and insoluble and soluble fiber in an effective ratio of insoluble to soluble fiber. The compositions comprise effective amounts of n-3 fatty acids, antioxidants and insoluble and soluble fiber in an effective ratio of insoluble to soluble fiber. In some embodiments, the effective amount of n-3 fatty acids is 0.6-0.9% of daily nutritional intake, and in some embodiments 0.65-0.85% of daily nutritional intake, and in some embodiments 0.70-0.80% of daily nutritional intake, and in some embodiments 0.72-0.79% of daily nutritional intake. In some embodiments, the effective amount of antioxidants comprises a combination of vitamin C and vitamin E. In some embodiments, in the combination of vitamin C and vitamin E, the effective amount of vitamin C is at level above 400 ppm of daily nutritional intake, and in some embodiments at level above 450 ppm of daily nutritional intake, and in some embodiments at level above 475 ppm of daily nutritional intake, and in some embodiments at level above 480 ppm of daily nutritional intake, and in some embodiments at level above 490 ppm of daily nutritional intake, and in some embodiments at level above 500 ppm of daily nutritional intake, and in some embodiments at level above 550 ppm of daily nutritional intake. In some embodiments, in the combination of vitamin C and vitamin E, the effective amount of vitamin E is at level above 1000 IU/kg of daily nutritional intake, and in some embodiments the effective amount of vitamin E is at level above 1200 IU/kg of daily nutritional intake, and in some embodiments the effective amount of vitamin E is at level above 1300 IU/kg of daily nutritional intake, and in some embodiments the effective amount of vitamin E is at level above 1400 IU/kg of daily nutritional intake, and in some embodiments the effective amount of vitamin E is at level above 1500 IU/kg of daily nutritional intake. In some embodiments, a combination of insoluble fiber and soluble fiber is provided in an amount equal to 4.0% or more of daily nutritional intake, in some embodiments 4.5% or more of daily nutritional intake, in some embodiments 4.6% or more of daily nutritional intake, in some embodiments 4.7% or more of daily nutritional intake, in some embodiments 4.8% or more of daily nutritional intake, in some embodiments 4.9% or more of daily nutritional intake, in some embodiments 5.0% or more of daily nutritional intake, in a ratio of insoluble fiber to soluble fiber (amount of insoluble fiber/the amount of soluble fiber) in some embodiments in the range of between 2.0 and 3.0, and in some embodiments in a ratio is in the range of between 2.1 and 2.9, and in some embodiments in a ratio is in the range of between 2.2 and 2.8, and in some embodiments in a ratio in the range of between 2.3 and 2.7, and in some embodiments in a ratio in the range of between 2.4 and 2.6, and in some embodiments in a ratio in the range of between 2.4 and 2.5.

"Daily nutritional intake" and "total nutritional intake per day" refers to dry matter intake per day. That is, water weight is not included in calculating the amount of nutrition consumed per day. To the extent that food and food ingredient contain water/moisture, the dry matter represents everything in the sample other than water including protein, fiber, fat, minerals, etc. Dry matter weight is the total weight minus the weight of any water. Dry matter intake per day is calculated as the total nutritional intake per day excluding all water. For example, an amount of an ingredient equal to a specific percent of daily nutritional intake refers to the amount of that ingredient in dry matter form (i.e. excluding all water) relative to the total amount of dry matter consumed (also excluding all water) in a day. The skilled artisan would readily recognize and understand nutritional amounts and percentages expressed as dry matter amounts, dry matter weights and dry matter percentages. Since foods, whether wet, moist or dry, generally contain as certain amount of water, when calculating daily dry matter intake, the water component of such food is excluded. To calculate total daily nutritional intake, which is dry matter intake per day, water is excluded. To calculate percent of an ingredient of total daily intake on a dry matter basis, water is removed from the total intake to give total daily dry matter intake and the percent of the ingredient is based on amount of ingredient present as dry matter.

The compositions useful in the methods may be a pet food composition such as a dog food composition. Alternatively, n-3 fatty acids, antioxidants and insoluble and soluble fiber may be administered as a supplement, a treat or toy or otherwise not incorporated into the food provided to the animal for daily nutritional intake.

In some preferred embodiments, the animal is a canine and the methods comprise administering to the canine effective amounts of n-3 fatty acids, antioxidants and insoluble and soluble fiber. The effective amount of n-3 fatty acids administered to the canine per day is 0.6-0.9% of daily nutritional intake, and in some embodiments 0.65-0.85% of daily nutritional intake, and in some embodiments 0.70-0.80% of daily nutritional intake, and in some embodiments 0.72-0.79% of daily nutritional intake.

The effective amount of antioxidants comprises a combination of vitamin C and vitamin E, and in some embodiments of the combination: the effective amount of vitamin C, based on daily nutritional intake, is at level above 400 ppm, in some embodiments at level above 450 ppm, in some embodiments at level above 475 ppm, in some embodiments at level above 480 ppm, in some embodiments at level above 490 ppm, in some embodiments at level above 500 ppm, and in some embodiments at level above 550 ppm; and the effective amount of vitamin E, based on daily nutritional intake, is at level above 1000 IU/kg, in some embodiments at level above 1200 IU/kg, in some embodiments at level above 1300 IU/kg, in some embodiments at level above 1400 IU/kg, and in some embodiments at level above 1500 IU/kg. A combination of insoluble fiber and soluble fiber is provided in an effective amount, based on daily nutritional intake, in an amount equal to 4.0% or more, in some embodiments 4.5% or more, in some embodiments 4.6% or more, in some embodiments 4.7% or more, in some embodiments 4.8% or more, in some embodiments 4.9% or more, in some embodiments 5.0% or more, and in a ratio of insoluble fiber to soluble fiber (amount of insoluble fiber/the amount of soluble fiber) in some embodiments in the range of between 2.0 and 3.0, in some embodiments in a ratio between 2.1 and 2.9, in some embodiments in a ratio between 2.2 and 2.8, in some embodiments in a ratio between 2.3 and 2.7, in some embodiments in a ratio between 2.4 and 2.6, and in some embodiments in a ratio between 2.4 and 2.5. The compositions preferably are dog food compositions that comprise the daily effective amounts of n-3 fatty acids, antioxidants such as the combination of vitamin C and vitamin E and a combination of soluble and insoluble fiber.

Compositions and methods for the treatment of anxiety or stress in an animal, particularly in companion animals such as felines and canines, are provided. The compositions and methods are useful to treat a symptom of anxiety or stress in such animals that are in need thereof. The compositions and methods are useful to treat a symptom of anxiety or stress in such animals that have elevated levels of 4-EPS. The compositions and methods are useful to reduce elevated levels of 4-EPS in an animal that has elevated levels of 4-EPS, such as companion animals, particularly canines. In some embodiments, the compositions and methods for the treatment of canine anxiety or canine stress in a canine. Compositions and methods are provided which promote growth of desirable, beneficial microbes in gut microbial populations and inhibit growth of undesirable, unhealthy microbes in gut microbial populations.

As used herein, the term "treatment" refers to eliminating, reducing the severity or preventing one or more symptoms.

As used herein, the term "anxiety" refers to anxiety, anxiety disorders and symptoms of anxiety and anxiety disorders.

As used herein, the term "stress" refers to stress, stress disorders, and symptoms of stress and stress disorders.

As used herein, the terms "treatment" with reference to anxiety refers to therapeutic and/or prophylactic activity. In a canine with symptoms of anxiety, treatment of canine anxiety refers to eliminating symptoms, arresting or reducing progression of symptoms, reducing severity of symptoms and preventing symptoms. Treatment that initially eliminate, arrests, reduces progression of or reduces severity of symptoms may continue and the continuing treatment may further eliminate, arrests, reduces progression of or reduces severity of symptoms and/or prevent return or development of symptoms or reduce severity of further development of symptoms. In some embodiments, prior to treating for canine anxiety, a canine may be identified as having symptoms of anxiety. In some embodiments, a canine may be treated for anxiety without identifying symptoms of anxiety prior to treatment. In some embodiments, prior to treatment for anxiety, a canine may be identified as being predisposed to having or developing anxiety. In some embodiments, prior to treatment for anxiety, a canine may be identified as having elevated levels of 4-EPS.

As used herein, the terms "treatment" with reference to stress and stress disorders refers to therapeutic and/or prophylactic activity. In a canine with symptoms of stress or a stress disorder, treatment of canine stress refers to eliminating symptoms, arresting or reducing progression of symptoms, reducing severity of symptoms and preventing symptoms. Treatment that initially eliminate, arrests, reduces progression of or reduces severity of symptoms may continue and the continuing treatment may further eliminate, arrests, reduces progression of or reduces severity of symptoms and/or prevent return or development of symptoms or reduce severity of further development of symptoms. In some embodiments, prior to treating for canine stress, a canine may be identified as having symptoms of stress or a stress disorder. In some embodiments, a canine may be treated for stress or a stress disorder without identifying symptoms of anxiety prior to treatment. In some embodiments, prior to treatment for stress or a stress disorder, a canine may be identified as being predisposed to having or developing stress or a stress disorder. In some embodiments, prior to treatment for stress or a stress disorder, a canine may be identified as having elevated levels of 4-EPS.

As used herein, the terms "treatment" with reference to promoting beneficial microbial growth and inhibition of harmful microbial growth refers to therapeutic and/or prophylactic activity. In a canine with reduced levels of beneficial microbes and elevated levels of harmful microbes, treatment for arresting levels of beneficial microbes and harmful microbes or promoting beneficial microbial growth and inhibiting harmful microbial growth. A canine identified as being predisposed to inhibiting beneficial microbial growth and promoting harmful microbial growth prior to initiating treatment. Treatment that initially promotes beneficial microbial growth and inhibits harmful microbial growth in an animal with elevated levels of harmful microbes and reduced levels of beneficial microbes, increases levels of beneficial microbes and decreases levels of harmful microbes to a more healthful balance and thereafter the continuing treatment maintains levels. In some embodiments, prior to treating for canine stress, a canine may be identified as having elevated levels of harmful microbes and reduced levels of beneficial microbes. In some embodiments, a canine may be treated without identifying elevated levels of harmful microbes and reduced levels of beneficial microbes in the animal.

As used herein the terms "treatment of elevated 4-EPS", "treating for elevated 4-EPS" and "treating elevated 4-EPS" refer to therapeutic and/or prophylactic activity in which 4-EPS levels are reduced. In a canine with elevated 4-EPS levels, "treatment of elevated 4-EPS", "treating for elevated 4-EPS" and "treating elevated 4-EPS" refers to reducing elevated 4-EPS levels. Treatment may lower elevated 4-EPS levels to normal, non-elevated levels or to reduced elevated 4-EPS levels. Following reduction of elevated 4-EPS levels, treatment may prevent elevation of 4-EPS levels or reduce severity of further development of elevated 4-EPS levels. In a canine that does not have elevated 4-EPS levels, "treatment of elevated 4-EPS", "treating for elevated 4-EPS" and "treating elevated 4-EPS" refers to arresting or lowering of 4-EPS levels, and preventing development of elevated 4-EPS levels or reducing severity of development of elevated 4-EPS levels. In some embodiments, prior to treating for 4-EPS, a canine may be identified as having elevated 4-EPS by measuring 4-EPS levels. In some embodiments, a canine may be treated for elevated 4-EPS without measuring 4-EPS levels prior to treatment. In some embodiments, prior to treating for 4-EPS, a canine may be identified as being predisposed to elevated 4-EPS. A canine identified as being predisposed to elevated 4-EPS may at the time of treatment have elevated 4-EPS, in which case the treatment is therapeutic, or may not have elevated 4-EPS, in which case the treatment is prophylactic, or treatment may be undertaken without determining 4-EPS levels. In some embodiments, a canine may be identified as being predisposed to elevated 4-EPS prior to initiating treatment with or without measuring 4-EPS levels.

As used herein, "an amount effective," "an effective amount," and like terms refer to that amount of n-3 fatty acids and antioxidants effective to achieve a particular biological result, i.e., treatment of elevated levels of 4-EPS, anxiety, stress, and levels of beneficial and harmful microbes in the microbiome when delivered in combination with an effective ratio of insoluble to soluble fiber. In specific embodiments, administration of a composition comprising an effective amount of n-3 fatty acids and antioxidants in combination with an effective ratio of insoluble to soluble fiber will be undertaken for a time sufficient to effect treatment. In a particular embodiment, the method comprises administration and consumption of a composition comprising an effective amount of n-3 fatty acids and antioxidants in combination with an effective ratio of insoluble to soluble fiber for a period of time sufficient to result in effective treatment and maintenance An effective amount may be based on several factors, including a dog's ideal weight, the age, gender, level of activity, the metabolizable energy of the composition, and the frequency of feeding the compositions, e.g., once, twice, or three times daily, and other compositions fed to the dog. In some embodiments an effective amount refers to an amount of n-3 fatty acids and antioxidants in combination with an effective ratio of insoluble to soluble fiber administered based upon total nutritional intake per day. In some embodiments an effective amount refers to a pet food comprising, on a dry matter basis for total nutritional intake per day, n-3 fatty acids and antioxidants in combination with an effective ratio of insoluble to soluble fiber. That is, the amount of food suitable to meet all daily nutrition and energy requirements for a canine subject contains, on a dry matter basis, effective amounts of n-3 fatty acids and antioxidants in combination with an effective ratio of insoluble to soluble fiber.

As used herein, "an effective ratio of insoluble to soluble fiber" and like terms refer to that the ration of insoluble fiber to soluble fiber in a daily diet that is effective to achieve a particular biological result, i.e., treatment of elevated levels of 4-EPS, anxiety, stress, and levels of beneficial and harmful microbes in the microbiome when delivered in combination with an effective amounts of n-3 fatty acids and antioxidants. An effective ratio may be based on several factors, including a dog's ideal weight, the age, gender, level of activity, the metabolizable energy of the composition, and the frequency of feeding the compositions, e.g., once, twice, or three times daily, and other compositions fed to the dog. An effective ratio may be expressed as a number calculated by dividing the amount of insoluble fiber by the amount of soluble fiber (i.e. amount of insoluble fiber/the amount of soluble fiber).

In specific embodiments, administration of a composition comprising an effective amount of n-3 fatty acids and antioxidants in combination with insoluble fiber and soluble fiber in an effective ratio of insoluble to soluble fiber will be undertaken for a time sufficient to effect treatment. In a particular embodiment, the method comprises administration and consumption of a composition comprising an effective amount of n-3 fatty acids and antioxidants in combination with insoluble fiber and soluble fiber in an effective ratio of insoluble to soluble fiber for a period of time sufficient to result in effective treatment and maintenance.

In some embodiments, the effective amount of n-3 fatty acids is 0.6-0.9%, of daily nutritional intake, and in some embodiments 0.65-0.85%, of daily nutritional intake, and in some embodiments 0.70-0.80%, of daily nutritional intake, and in some embodiments 0.72-0.79%, of daily nutritional intake.

In some embodiments, the effective amount of antioxidants comprises a combination of vitamin C and vitamin E. In some embodiments, in the combination of vitamin C and vitamin E, the effective amount of vitamin C is at level above 400 ppm of daily nutritional intake, and in some embodiments at level above 450 ppm of daily nutritional intake, and in some embodiments at level above 475 ppm of daily nutritional intake, and in some embodiments at level above 480 ppm of daily nutritional intake, and in some embodiments at level above 490 ppm of daily nutritional intake, and in some embodiments at level above 500 ppm of daily nutritional intake, and in some embodiments at level above 550 ppm of daily nutritional intake. In some embodiments, in the combination of vitamin C and vitamin E, the effective amount of vitamin E is at level above 1000 IU/kg of daily nutritional intake, and in some embodiments the effective amount of vitamin E is at level above 1200 IU/kg of daily nutritional intake, and in some embodiments the effective amount of vitamin E is at level above 1300 IU/kg of daily nutritional intake, and in some embodiments the effective amount of vitamin E is at level above 1400 IU/kg of daily nutritional intake, and in some embodiments the effective amount of vitamin E is at level above 1500 IU/kg of daily nutritional intake.

In some embodiments, a combination of insoluble fiber and soluble fiber is provided in an amount equal to 4.0% or more of daily nutritional intake, in some embodiments 4.5% or more of daily nutritional intake, in some embodiments 4.6% or more of daily nutritional intake, in some embodiments 4.7% or more of daily nutritional intake, in some embodiments 4.8% or more of daily nutritional intake, in some embodiments 4.9% or more of daily nutritional intake, in some embodiments 5.0% or more of daily nutritional intake, in a ratio of insoluble fiber to soluble fiber (amount of insoluble fiber/the amount of soluble fiber) in some embodiments in the range of between 2.0 and 3.0, and in some embodiments in a ratio is in the range of between 2.1 and 2.9, and in some embodiments in a ratio is in the range of between 2.2 and 2.8, and in some embodiments in a ratio in the range of between 2.3 and 2.7, and in some embodiments in a ratio in the range of between 2.4 and 2.6, and in some embodiments in a ratio in the range of between 2.4 and 2.5.

In some preferred embodiments, the animal is a canine and the methods comprise administering to the canine a combination of effective amounts n-3 fatty acids, antioxidants, such as vitamin C and vitamin E and insoluble and soluble fiber in an effective ratio. The combination may be administered as a pet food composition such as a dog food composition or as a supplement, a treat or toy or otherwise not incorporated into the food provided to the animal for daily nutritional intake. In some embodiments, the effective amount of n-3 fatty acids is 0.6-0.9%, of daily nutritional intake, and in some embodiments 0.65-0.85%, of daily nutritional intake, and in some embodiments 0.70-0.80%, of daily nutritional intake, and in some embodiments 0.72-0.79%, of daily nutritional intake.

A "food," "food composition," or "pet food composition" can, in some embodiments, be a nutritionally complete diet for the animal, such as a dog, to which it is fed.

As used herein, an "ingredient" refers to any component of a composition.

The term "nutrient" refers to a substance that provides nourishment. In some cases, an ingredient may comprise more than one "nutrient," for example, a composition may comprise corn comprising important nutrients including both protein and carbohydrate.

Food compositions can be provided to an animal, such as but not limited to a pet, in the form of pet food. A variety of commonly known types of pet foods are available to pet owners. The selection of pet food includes but is not limited to wet pet food, semi-moist pet food, dry pet food and pet treats. Wet pet food generally has a moisture content greater than about 65%. Semi-moist pet food typically has a moisture content between about 20% and about 65% and may include humectants, potassium sorbate, and other ingredients to prevent microbial growth (bacteria and mold). Dry pet food such as but not limited to food kibbles generally has a moisture content below about 15%. Pet treats typically may be semi-moist, chewable treats; dry treats in any number of forms, chewable bones or baked, extruded or stamped treats; confection treats; or other kinds of treats as is known to one skilled in the art.

As used herein, the term "kibble" or "food kibble" refers to a particulate pellet like component of animal feeds, such as dog and cat feeds. In some embodiments, a food kibble has a moisture, or water, content of less than 15% by weight. Food kibbles may range in texture from hard to soft. Food kibbles may range in internal structure from expanded to dense. Food kibbles may be formed by an extrusion process or a baking process. In non-limiting examples, a food kibble may have a uniform internal structure or a varied internal structure. For example, a food kibble may include a core and a coating to form a coated kibble. It should be understood that when the term "kibble" or "food kibble" is used, it can refer to an uncoated kibble or a coated kibble.

As used herein, the term "extrude" or "extrusion" refers to the process of sending preconditioned and/or prepared ingredient mixtures through an extruder. In some embodiments of extrusion, food kibbles are formed by an extrusion processes wherein a kibble dough, including a mixture of wet and dry ingredients, can be extruded under heat and pressure to form the food kibble. Any type of extruder can be used, examples of which include but are not limited to single screw extruders and twin-screw extruders. The list of sources, ingredients, and components as described hereinafter are listed such that combinations and mixtures thereof are also contemplated and within the scope herein.

As contemplated herein, compositions are meant to encompass, but not be limited to, nutritionally-complete and balanced animal food compositions. A "nutritionally complete diet" is a diet that includes sufficient nutrients for maintenance of normal health of a healthy dog on the diet. Nutritionally complete and balanced pet food compositions, e.g., for canines, are familiar to one of skill in the art. For example, substances such as nutrients and ingredients suitable for nutritionally complete and balanced animal feed compositions, and recommended amounts thereof, may be found for example, in the Official Publication of the Association of American Feed Control Officials, Inc. (AAFCO), Atlanta, Ga., (2012).

It is contemplated that in feeding a dog a diet comprising an effective amount of n-3 fatty acids and antioxidants in combination with insoluble fiber and soluble fiber an effective ratio of insoluble to soluble fiber, a preferred method comprises feeding the dog a food that contains an effective amount of n-3 fatty acids and antioxidants in combination with insoluble fiber and soluble fiber in an effective ratio of insoluble to soluble fiber. In other embodiments, feeding a dog a diet comprising an effective amount of n-3 fatty acids and antioxidants in combination with insoluble fiber and soluble fiber in an effective ratio of insoluble to soluble fiber is achieved by administering the dog the n-3 fatty acids, antioxidants and insoluble and insoluble fiber as a supplement or treat. Whether delivered in a pet food composition or as a separate supplement or in a treat, providing the dog with the effective amount of n-3 fatty acids and antioxidants in combination with insoluble fiber and soluble fiber in the effective ratio of insoluble to soluble fiber by any means is considered feeding a dog a diet comprising an effective amount of n-3 fatty acids and antioxidants in combination with an effective ratio of insoluble to soluble fiber.

As used herein, the term "supplement(s)" include, but are not limited to, a feed used with another feed to improve nutritive balance or performance of the total diet for an animal. Supplements include, but are not limited to, compositions that are fed undiluted as a supplement to other feeds, offered free choice with other parts of an animal's ration that are separately available, or diluted and mixed with an animal's regular feed to produce a complete feed. The AAFCO guidelines, for example, contain a discussion relating to supplements in the Official Publication of the Association of American Feed Control Officials, Inc. (AAFCO), Atlanta, Ga. (2012). Supplements may be in various forms including, for example, powders, liquids, syrups, pills, encapsulated compositions and the like A diet may comprise an effective amount of n-3 fatty acids and antioxidants in combination with insoluble fiber and soluble fiber in an effective ratio of insoluble to soluble fiber reduces elevated levels of 4-EPS in an animal such as a feline or a canine. A diet that comprises an effective amount of n-3 fatty acids and antioxidants in combination with insoluble fiber and soluble fiber in an effective ratio of insoluble to soluble fiber is useful to treat anxiety in a canine. A diet that comprises an effective amount of n-3 fatty acids and antioxidants in combination with insoluble fiber and soluble fiber in an effective ratio of insoluble to soluble fiber is useful to treat stress in a canine. A diet that comprises an effective amount of n-3 fatty acids and antioxidants in combination with insoluble fiber and soluble fiber in an effective ratio of insoluble to soluble fiber is useful to promote of beneficial microbial growth and inhibit harmful microbial growth in the animal's microbiome, particularly a microbiome of the animal's gastrointestinal track, and particularly in an animal that is a feline or canine.

Compositions and Formulations

Application of the methodology outlined above has identified a combination of effective amounts of n-3 fatty acids and antioxidants with an effective ratio of insoluble fiber to soluble fiber that provide significant benefits to animals, particularly dogs and cats, identified as being predisposed to elevated levels of 4-EPS and thus at an increased risk of developing anxiety, an increased risk of developing anxiety stress and an increased risk of inhibiting beneficial microbial growth and promoting harmful microbial growth in the canine's microbiome, in particular the gut microbiome. In some embodiments, the effective amount of n-3 fatty acids and antioxidants in combination with the effective ratio of insoluble to soluble fiber are components that have been combined with other ingredient to provide a nutritionally complete diet. In some embodiments, the food product is a nutritionally complete diet for an adult companion animal. In a specific aspect, the food product is a nutritionally complete diet formulated for an adult companion canine.

In some embodiments, the compositions include food compositions is suitable for consumption by a companion animal, particularly a dog, that comprise an effective amount of n-3 fatty acids and antioxidants in combination with an effective ratio of insoluble to soluble fiber, together with protein and/or fat and/or carbohydrate. In some embodiments, for example, in addition to n-3 fatty acids, antioxidants, insoluble fiber and soluble fiber, a nutritionally complete and balanced dog food composition may comprise: from 4% to 90%, from 4% to 75%, from 5% to 75%, from 10% to 60% protein, or from 15% to 50% by weight of protein based on the total weight of the composition on a dry matter basis; from 0% to 90%, from 2% to 80%, from 5% to 75%, and from 10% to 50% by weight of carbohydrate based on the total weight of the composition on a dry matter basis; and from 2% to 60%, from 5% to 50%, and from 10% to 35% by weight of fat based on the total weight of the composition on a dry matter basis. In some embodiments, for example, in addition to n-3 fatty acids, antioxidants, insoluble fiber and soluble fiber, a nutritionally complete and balanced dog food composition may further contain from 0 to 15% or from 2% to 8%, by weight of other vitamins, and minerals, antioxidants, and other nutrients, e.g. amino acids which support the nutritional needs of the animal.

The compositions comprise at least one n-3 fatty acid, otherwise referred to as an omega-3 fatty acid. Omega-3 fatty acids, also called n-3 fatty acids, are a recognized group of polyunsaturated fatty carboxylic acids, also referred to as polyunsaturated fatty acids (PUFAs). Omega-3-fatty acids are characterized by the presence of a double bond between carbon atoms t3 and 4 as measured from the end of the molecule not containing the carboxy group, i.e. three atoms away from the terminal methyl group in their chemical structure. They have long chain polyalkenyl groups, which are normal or branched, with about 8 to about 24 carbon atoms, preferably about 10 to about 22 carbon atoms, including the carbon atom of the carboxyl group.

Examples of omega-3 fatty acids include, but are not limited to, alpha-linoleic acid (ALA), docosahexanoic acid (DHA), eicosapentaenoic acid (EPA) and octadecatetraenoic acid. In some embodiments, the composition comprises one of ALA, DHA or EPA. In some embodiments, the composition comprises at least two of ALA, DHA or EPA. In some embodiments, the composition comprises all three of ALA, DHA and EPA. Omega-3-fatty acids are typically, exemplified by EPA and DHA are generally considered to be the most important and significant of the long chain omega-3 fatty acids. Generally, these long chain fatty acids are present in relatively low, almost minute, quantities or completely absent in typical pet food compositions. The fatty acid composition of foods consumed by companion pets, for example dogs and cats, directly influences the biological levels of fatty acid found in their blood. Natural products which have relatively high levels of omega-3 unsaturated fatty acids such as EPA and DHA can be derived from marine oils such as salmon, anchovy, sardine and menhaden. Such natural oils can be concentrated to even higher percentages of omega-3-fatty acids.

Derivatives of omega-3 fatty acids can also be employed. Many types of derivatives are well known to one skilled in the art. Examples of Suitable derivatives are esters, such as branched or unbranched and/or saturated or unsaturated C—C cycloalkyl esters, in particular C—C alkyl esters. Their systemic potential has been recognized in the art, for example U.S. Pat. Nos. 5,776,913 and 6,015,798. As used in this application and claims "omega-3 fatty acid includes its derivatives.

With respect to the quantity of the omega-3 fatty acid or mixture of omega-3 fatty acids, in some embodiments 0.6-0.9 wt % dry matter basis per daily nutritional intake, and in some embodiments 0.65-0.85% dry matter basis per daily nutritional intake, and in some embodiments 0.70-0.80% dry matter basis per daily nutritional intake, and in some embodiments 0.72-0.79% dry matter basis per daily nutritional intake as measured by quantity of daily diet composition should be administered. In some embodiments, EPA and DHA are the preferred omega-3 fatty acids.

In some embodiments, methods comprise administering total fatty acids in an amount equal to about 10-15 wt % dry matter basis per daily nutritional intake, and in some embodiments 11-14% dry matter basis per daily nutritional intake, and in some embodiments 12-13% dry matter basis per daily nutritional intake, and in some embodiments 12.1-12.6 wt % dry matter basis per daily nutritional intake, and in some embodiments 12.2-12.4 wt % dry matter basis per daily nutritional intake. Percent n-3 fatty acids to total fatty acids may be 4.0-8.5%, and in some embodiments be 4.5-8.0%, in some embodiments be 5.0-7.5%, in some embodiments be 5.5-7.0%, in some embodiments be 5.5-6.5%.

The compositions also comprise at least one antioxidant. Antioxidants are well known in the art. Examples of antioxidants include but are not limited to vitamin C, vitamin E (tocopherols and/or tocotrienols), glutathione, lipoic acid, melatonin, carnitine and beta-carotene. In some embodiments, the compositions comprise at least one of vitamin C, vitamin E (tocopherols and/or tocotrienols), glutathione, lipoic acid, melatonin, or beta-carotene. In some embodiments, the compositions comprise at least two of vitamin C, vitamin E (tocopherols and/or tocotrienols), glutathione, lipoic acid, melatonin, or beta-carotene. In some embodiments, the compositions comprise at least three of vitamin C, vitamin E (tocopherols and/or tocotrienols), glutathione, lipoic acid, melatonin, or beta-carotene. In some embodiments, the compositions comprise at least four of vitamin C, vitamin E (tocopherols and/or tocotrienols), glutathione, lipoic acid, melatonin, or beta-carotene. In some embodiments, the compositions comprise at least five or more of vitamin C, vitamin E (tocopherols and/or tocotrienols), glutathione, lipoic acid, melatonin, and/or beta-carotene. In some embodiments, the compositions comprise at vitamin C and vitamin E. Vitamin C can be administered in this diet as ascorbic acid and its various derivatives thereof such as calcium phosphate salts, cholesteryl salt, 2-monophosphate, and the like which will function in a vitamin C like activity after ingesting by the pet. They can be in any form, e.g. liquid, semisolid, solid and heat stable form.

Vitamin C may be provided at level above 400 ppm of daily nutritional intake, in some embodiments at level above 450 ppm of daily nutritional intake, in some embodiments at level above 475 ppm of daily nutritional intake, in some embodiments at level above 480 ppm of daily nutritional intake, in some embodiments at level above 490 ppm of daily nutritional intake, and in some embodiments at level above 500 ppm of daily nutritional intake, and in some embodiments at level above 550 ppm of daily nutritional intake. Vitamin E may be provided at level above 1000 IU/kg of daily nutritional intake, in some embodiments at level above 1200 IU/kg of daily nutritional intake, and in some embodiments at level above 1300 IU/kg of daily nutritional intake, and in some embodiments at level above 1400 IU/kg of daily nutritional intake, and in some embodiments at level above 1500 IU/kg of daily nutritional intake.

Dietary fiber refers to the components of plants which are resistant to digestion by the animal's digestive enzymes. The dietary fiber content of a composition may be determined by any number of methods known by those of skill in the art, such as those published by the OMA. Dietary fiber includes soluble and insoluble fiber.

Soluble fiber is resistant to digestion and absorption in the small intestine but undergoes complete or partial fermentation in the large intestine. Examples of soluble fiber sources include beet pulp, guar gum, chicory root, *psyllium*, pectin, blueberry, cranberry, squash, apples, oats, beans, citrus, barley, and peas. Insoluble fiber may be supplied by any of a variety of sources, including cellulose, whole wheat products, wheat oat, corn bran, flax seed, grapes, celery, green beans, cauliflower, potato skins, fruit skins, vegetable skins, peanut hulls, and soy fiber. Crude fiber includes indigestible components contained in cell walls and cell contents of plants such as grains, e.g., hulls of grains such as rice, corn, and beans. The crude fiber content of a composition may be determined by any number of methods known by those of skill in the art. preferably OMA method 991.43/32.1.17 (1994).

A combination of insoluble fiber and soluble fiber may be provided in an amount equal to 4.0 wt % dry matter basis or more per daily nutritional intake, in some embodiments 4.5 wt % dry matter basis or more per daily nutritional intake, in some embodiments 4.6 wt % dry matter basis or more per daily nutritional intake, in some embodiments 4.7 wt % dry matter basis or more per daily nutritional intake, in some embodiments 4.8 wt % dry matter basis or more per daily nutritional intake, in some embodiments 4.9 wt % dry matter basis or more per daily nutritional intake, in some embodiments 5.0 wt % dry matter basis or more per daily nutritional intake, in a ratio of insoluble fiber to soluble fiber (amount of insoluble fiber/the amount of soluble fiber) in some embodiments in the range of between 2.0 and 3.0, and in some embodiments in a ratio is in the range of between 2.1 and 2.9, and in some embodiments in a ratio is in the range of between 2.2 and 2.8, and in some embodiments in a ratio in the range of between 2.3 and 2.7, and in some embodiments in a ratio in the range of between 2.4 and 2.6, and in some embodiments in a ratio in the range of between 2.4 and 2.5.

In some embodiments, composition used in the methods comprise crude fiber in an amount equal to 0.6-1.4 wt % dry matter basis or more per daily nutritional intake, in an amount equal to 0.7-1.3 wt % dry matter basis or more per daily nutritional intake, in an amount equal to 0.8-1.2 wt % dry matter basis or more per daily nutritional intake, in an amount equal to 0.9-1.1 wt % dry matter basis or more per daily nutritional intake, in an amount equal to about 1.0 wt % dry matter basis or more per daily nutritional intake.

Sources of proteins, carbohydrates, fats, vitamins, minerals, balancing agents, and the like, suitable for inclusion in the compositions, and particularly in the food products to be administered in methods provided herein, may be selected from among those conventional materials known to those of ordinary skill in the art.

Proteins useful as ingredients of the food compositions may comprise proteins from animal sources, such as animal proteins, including mammalian, avian protein, reptilian, amphibian, fish, invertebrate proteins and combinations thereof; e.g., from any of cattle, sheep, pig, goat, deer, rabbit, horse, kangaroo, their milk, curds, whey or blood, and internal tissues and organs such as smooth muscle, striate muscle, liver, kidney, intestine or heart; chicken including internal tissues and organs such as smooth muscle, striate muscle, liver, kidney, intestine or heart and chicken eggs, additional avian protein sources encompass turkey, goose, duck, ostrich, quail, pigeon, their eggs and internal tissues and organs such as smooth muscle, striate muscle, liver, kidney, intestine or heart; amphibian sources include frog or salamander, reptilian protein sources include alligator, lizard, turtle and snake; a fish protein sources include catfish, herring, salmon, tuna, bluefish, cod, halibut, trout, swordfish and their eggs; and an invertebrate protein sources include lobster, crab, clams, mussels or oysters, and combinations thereof, meat protein isolate, whey protein isolate, egg protein, mixtures thereof, and the like, as well as vegetable sources, such as corn gluten meal, wheat gluten, mixtures thereof, and the like.

In some embodiments, carbohydrates useful as ingredients of the food compositions may include but are not limited to, one or more of corn, whole yellow corn, grain sorghum, wheat, barley, rice, millet, brewers rice, oat groats, and polysaccharides (e.g., starches and dextrins) and sugars (e.g., sucrose, lactose, maltose, glucose, and fructose) that are metabolized for energy when hydrolyzed. Examples of additional carbohydrate sources suitable for inclusion in the compositions disclosed herein include, fruits and vegetables.

Fats useful as ingredients of the food compositions may be from any source, such as but not limited to poultry fat, beef tallow, lard, choice white grease, soybean oil, corn oil, canola oil, sunflower oil, mixtures thereof, and the like. The fat may be incorporated completely within the food composition, deposited on the outside of the food composition, or a mixture of the two methods.

In some embodiments, the compositions further include an effective amount of one or more substances selected from the group consisting of glucosamine, chondroitin, chondroitin sulfate, methylsulfonylmethane ("MSM"), creatine, antioxidants, *Perna canaliculata*, omega-3 fatty acids, omega-6 fatty acids and mixtures thereof.

In some embodiments, the food composition further comprises one or more amino acid such as but not limited to arginine, histidine, isoleucine, leucine, lysine, methionine (including DL-methionine, and L-methionine), phenylalanine, threonine, tryptophan, valine, taurine, carnitine, alanine, aspartate, cystine, glutamate, glutamine, glycine, proline, serine, tyrosine, and hydroxyproline.

In some embodiments, the food composition further comprises one or more fatty acids in addition to the omega-3 fatty acids discussed above, such as but not limited to lauric acid, myristic acid, palmitic acid, palmitoleic acid, margaric acid, margaroleic acid, stearic acid, oleic acid, linoleic acid, gadoleic acid, arachidonic acid, behenic acid, erucic acid, docosatetra acid.

In some embodiments, the food composition further comprises one or more macro nutrients such as but not limited to moisture, protein, fat, crude fiber, ash, dietary fiber, soluble fiber, insoluble fiber, raffinose, and stachyose.

In some embodiments, the food composition further comprises one or more micro nutrients such as but not limited to beta-carotene, alpha-lipoic acid, glucosamine, chondroitin sulfate, lycopene, lutein, and quercetin.

In some embodiments, the food composition further comprises one or more minerals such as but not limited to calcium, phosphorus, potassium, sodium, chloride, iron, copper, copper, manganese, zinc, iodine, selenium, selenium, cobalt, sulfur, fluorine, chromium, boron, and oxalate.

In some embodiments, the food composition further comprises stabilizing substances, for example, substances that tend to increase the shelf life of the composition. Potentially suitable examples of such substances include, for example, preservatives, antioxidants, synergists and sequestrants, packaging gases, stabilizers, emulsifiers, thickeners, gelling agents, and humectants. Examples of emulsifiers and/or thickening agents include, for example, gelatin, cellulose ethers, starch, starch esters, starch ethers, and modified starches.

In some embodiments, the food composition further comprises additives for coloring, palatability, and nutritional purposes include, for example, colorants; iron oxide, sodium chloride, potassium citrate, potassium chloride, and other edible salts; vitamins; minerals; and flavoring. The amount of such additives in a composition typically is up to 5% (dry basis of the composition).

Preparation of Compositions

The compositions that comprise the n-3 fatty acids, antioxidants, insoluble fiber and soluble fiber as outlined above may be prepared as food products suitable for consumption by dogs. These food products may be of any consistency or moisture content; i.e., the compositions may be moist, semi-moist, or dry food products. "Moist" food products are generally those with a moisture content of from 60% to 90% or greater. "Dry" food products are generally those with a moisture content of from 3% to 11%, and are often manufactured in the form of small pieces or kibbles. "Semi-moist food products generally have a moisture content of from 25% to 35%. The food products may also include components of more than one consistency, for example, soft, chewy meat-like particles or pieces as well as kibble having an outer cereal component or coating and an inner "cream" component.

In some embodiments, the food products that the n-3 fatty acids, antioxidants, insoluble fiber and soluble fiber as outlined above may be prepared in a canned or wet form using conventional food preparation processes known to those of ordinary skill in the art. Typically, ground animal proteinaceous tissues are mixed with the other ingredients, such as cereal grains, suitable carbohydrate sources, fats, oils, and balancing ingredients, including special purpose additives such as vitamin and mineral mixtures, inorganic salts, cellulose, beet pulp and the like, and water in an amount sufficient for processing. The ingredients are mixed in a vessel suitable for heating while blending the components. Heating the mixture is carried out using any suitable manner, for example, direct steam injection or using a vessel fitted with a heat exchanger. Following addition of all of the ingredients of the formulation, the mixture is heated to a temperature of from 50° F. to 212° F. Although temperatures outside this range can be used, they may be commercially-impractical without the use of other processing aids. When heated to the appropriate temperature, the material will typically be in the form of thick liquid, which is dispensed into cans. A lid is applied and the container is hermetically sealed. The sealed can is then placed in convention equipment designed for sterilization of the contents. Sterilization is usually accomplished by heating to temperatures of greater than 230° C. for an appropriate time depending on the temperature used, the nature of the composition, and related factors. The compositions and food products of the present invention can also be added to or combined with food compositions before, during, or after their preparation.

In some embodiments, the food products may be prepared in a dry form using convention processes known to those of ordinary skill in the art. Typically, dry ingredients, including dried animal protein, plant protein, grains and the like are ground and mixed together. Liquid or moist ingredients, including fats, oils water, animal protein, water, and the like are added combined with the dry materials. The specific formulation, order of addition, combination, and methods and equipment used to combine the various ingredients can be selected from those known in the art. For example, in certain embodiments, the resulting mixture is process into kibbles or similar dry pieces, which are formed using an extrusion process in which the mixture of dry and wet ingredients is subjected to mechanical work at high pressure and temperature, forced through small openings or apertures, and cut off into the kibbles, e.g., with a rotating knife. The resulting kibble can be dried and optionally coated with one or more topical coatings comprising, e.g., flavors, fats, oils, powdered ingredients, and the like. Kibbles may also be prepared from dough by baking, rather than extrusion, in which the dough is placed into a mold before dry-heat processing.

In preparing a composition, any ingredient generally may be incorporated into the composition during the processing of the formulation, e.g., during and/or after mixing of the other components of the composition. Distribution of these components into the composition can be accomplished by conventional means. In certain embodiments, ground animal and/or poultry proteinaceous tissues are mixed with other ingredients, including nutritional balancing agents, inorganic salts, and may further include cellulose, beet pulp, bulking agents and the like, along with sufficient water for processing.

In some embodiments, the compositions are formulated so as to be easier to chew. In specific embodiments, the compositions and food products are formulated to address specific nutritional differences between species and breeds of animals, as well as one of more of the attributes of the animal. For example, canine foods, for example, are typically formulated based upon the life stage, age, size, weight, body composition, and breed.

In another embodiment, treats comprising an effective amount of the n-3 fatty acids, antioxidants, insoluble fiber and soluble fiber as outlined above can be prepared by, for example, an extrusion or baking process similar to those described below for dry food to provide an edible product. Treats include, for example, compositions that are given to an animal to entice the animal to eat during a non-meal time. Treats may be nutritional, wherein the composition comprises one or more nutrients, and may, for example, have a composition as described above for food. Non-nutritional treats encompass any other treats that are non-toxic. Compositions can be coated onto the treat, incorporated into the treat, or both.

In another embodiment, an animal toy is provided that is a chewable or consumable toy. Such toys are typically prepared by coating any existing toy with effective amounts of the n-3 fatty acids, antioxidants, insoluble fiber and soluble fiber as outlined above. Toys therefore include, for example, chewable toys. Contemplated toys for dogs include, for example, artificial bones. In certain embodiments, the composition of the invention can form a coating on the surface of the toy or on the surface of a component of the toy, or it can be incorporated partially or fully throughout the toy, or both. A wide range of suitable toys are currently marketed. See, e.g., U.S. Pat. No. 5,339,771 (and references disclosed in U.S. Pat. No. 5,339,771). See also, e.g., U.S. Pat. No. 5,419,283 (and references disclosed in U.S. Pat. No. 5,419,283). It should be recognized that this invention contemplates both partially consumable toys (e.g., toys comprising plastic components) and fully consumable toys (e.g., rawhides and various artificial bones). It should be further recognized that this invention contemplates toys for companion animals and particularly for use by a cat or a dog.

All publications mentioned herein are incorporated by reference for the purpose of describing and disclosing the materials and methodologies that are reported in the publication, which might be used in connection with the invention.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

EXAMPLES

Example 1

The microbial metabolite, 4-ethylphenyl sulfate (4-EPS) is associated with stress and anxiety. Levels of 4-EPS in blood may be measured. Blood is collected in order to determine plasma metabolomic profiles. Levels of 4-EPS in plasma can be measured by a commercial laboratory (Metabolon, Durham, N.C., USA). Extracted supernatant is split and run on gas chromatography and liquid chromatography mass spectrometer platforms. The peak for 4-EPS is known and the area under the peak for each sample can be normalized to a known sample (See also: Evans, A. M., et al. (2009). Integrated, nontargeted ultrahigh performance liquid chromatography/electrospray ionization tandem mass spectrometry platform for the identification and relative quantification of the small-molecule complement of biological systems. Anal. Chem. 81, 6656-6667.) Gas chromatography (for hydrophobic molecules) and liquid chromatography (for hydrophilic molecules) are used to identify and provide relative quantification of metabolites such as 4-EPS present in plasma samples. (See also: Ballet, C. et al. (2018) New enzymatic and mass spectrometric methodology for the selective investigation of gut microbiota-derived metabolites, Chem. Sci. 9, 6233-6239; Akiyama, Y et al. (2012) A Metabolomic Approach to Clarifying the Effect of AST-120 on 5/6 Nephrectomized Rats by Capillary Electrophoresis with Mass Spectrometry (CE-MS) Toxins 4(11):1309-1322; and Kikuchi K, et al. (2010) Metabolomic search for uremic toxins as indicators of the effect of an oral sorbent AST-120 by liquid chromatography/tandem mass spectrometry. J Chromatogr B Analyt Technol Biomed Life Sci 878:2997-3002.)

A study was completed on 40 dogs that were each fed 3 different foods (prefeed, control and test) at different times. As shown in Table 1, the prefeed contained low soluble fiber, high insoluble fiber, low n-3 fatty acids and antioxidants and the control and the test foods each contained high soluble fiber, low insoluble fiber, high n-3 fatty acids and high antioxidants.

TABLE 1

Diet analysis results (%)

| Analyte | Prefeed | Control | Test |
| --- | --- | --- | --- |
| Crude fiber | 1.6 | 1 | 1 |
| Soluble fiber | 1.09 | 1.4 | 1.398 |
| Insoluble fiber | 4.23 | 3.49 | 3.34 |
| Insoluble fiber/Soluble fiber ratio | 3.88 | 2.49 | 2.39 |
| Crude fat | 13.35 | 13.91 | 13.59 |
| Crude protein | 18.76 | 21.35 | 21.48 |
| Total fatty acids | 12.51 | 12.26 | 12.31 |
| n-3 fatty acids | 0.4 | 0.72 | 0.79 |
| Percent n-3 fatty acids | 3.2 | 5.87 | 6.42 |
| Vitamin C (ppm) | 387.56 | 491.29 | 493.85 |
| Vitamin E (IU/kg) | 993.41 | 1,406.13 | 1,407.36 |
| Moisture | 8.14 | 8.96 | 8.08 |

The ratio of insoluble to soluble fiber of the prefeed, the control and the test foods were, 3.88%, 2.49% and 2.39%, respectively. The prefeed has total n-3 fatty acids percentage of 3.2. The percent total n-3 fatty acids in the control and the test foods were, 5.87 and 6.42, respectively.

All dogs were fed the prefeed during the first 30 days (days 0-30). Following initial prefeed period, the control group (20 dogs) received the control food for 30 days (days 31-60) while the test group (20 dogs) received the test food for 30 days (days 31-60). The animals then underwent a 30-day washout period (days 61-90) during which time they were fed prefeed. After the 30-day washout period on the prefeed, a 30-day cross-over (days 91-120) was performed to feed the groups with the food they did not receive before (control or test). That is, after completion of the washout period, dogs that were fed control food during days 31-60 were fed test food on days 91-120, and dogs that were fed test food during days 31-60 were fed control food on days 91-120.

Figure 1:
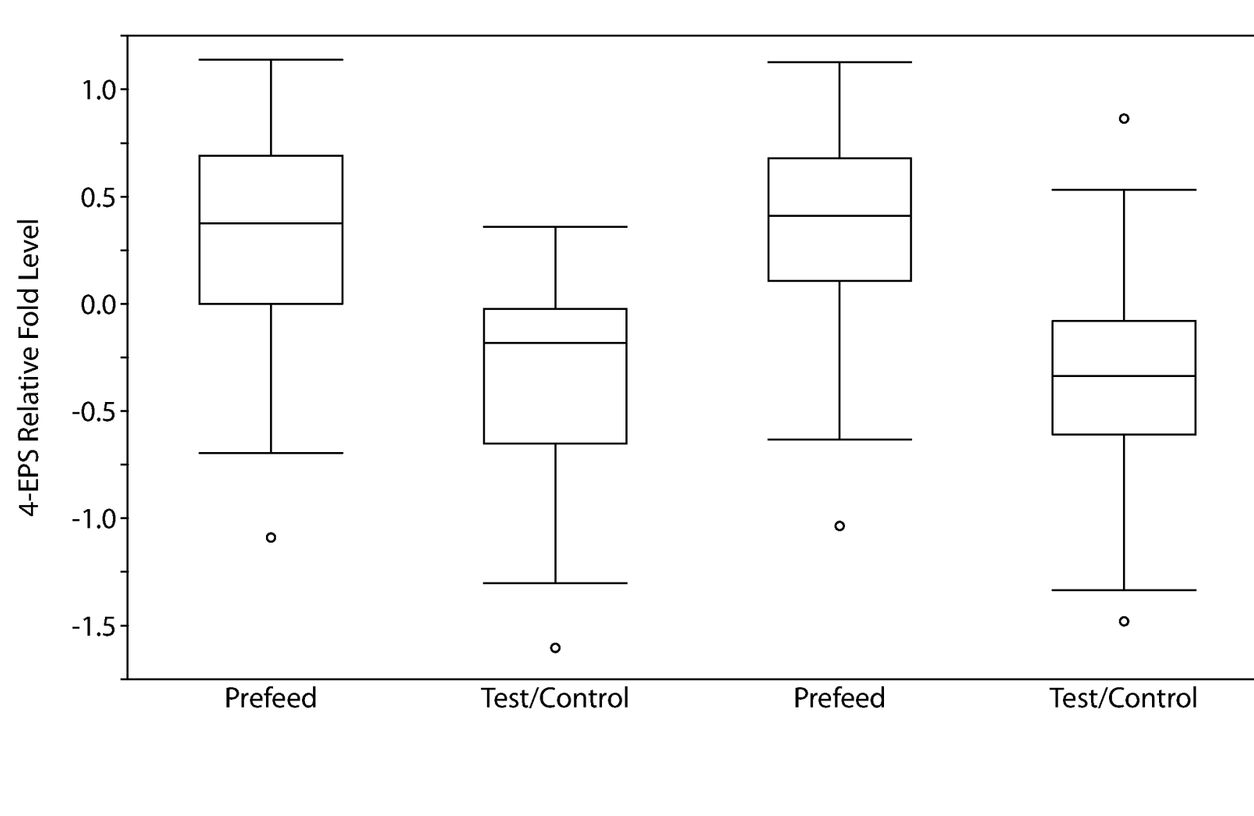
FIG. 1 shows data from experiments described in Example 1 in which 4-EPS levels were measured in dogs after being fed prefeed, control or test food compositions. The relative blood levels of log 4-EPS after each period of 30 days are shown for prefeed, control/test, washout (prefeed) and treatment after cross-over (control/test). The results show the prefeed led to significantly higher levels of 4-EPS compared to the treatment foods (control/test) (P<0.0001).

Samples were collected at the end of each 30 days period to compare levels of 4-EPS in blood and changes in the microbial composition in feces. Dogs had the highest 4-EPS levels on the prefeed food compared to the test or the control food (P<0.0001) (FIG. 1). There were certain microbial OTUs that were significantly different in abundance after the prefeed food compared to the test or the control food (Table 2). (OUT refers to operations taxonomic unit. OTUs are used to categorize bacteria based on sequence similarity.) These included the bacterial genera Odoribacter, Parabacteroides, Blautia and an unclassified genus in the family Pseudomonadaceae. All genera decreased after the consumption of the prefeed except the genus in the family Pseudomonadaceae, which was higher after the dogs ate the prefeed (Table 2). The genera Odoribacter, Parabacteroides, Blautia were negatively correlated with circulating levels of 4-EPS while the unclassified genus in the family Pseudomonadaceae was positively correlated to blood levels of 4-EPS (Table 3). There were no significant differences in the microbial composition after the test and the control food consumption.

In summary, the combination of insoluble and soluble fiber, n-3 fatty acids and antioxidants in the test and control foods (i.e. food containing insoluble to soluble fiber ratio of between 2.4 and 2.5; vitamin C and vitamin E levels above 400 ppm and above 1000 IU/kg, respectively; and percentage of total n-3 fatty acids between 5.5 and 6.5) decrease the level of the microbial stress-related metabolite, 4-EPS. This unique combination of fiber, antioxidants and n-3 fatty acids reduces 4-EPS by changing the gut microbial composition.

The canine microbial signature associated with the change in 4-EPS is identified. Fiber-fermenting microbes such as Parabacteroides, Blautia and Odoribacter negatively correlate with increased 4-EPS levels. The unclassified bacterial genus in the family Pseudomonadaceae has a positive correlation with circulating levels of 4-EPS and increased after the consumption of the prefeed.

Foods containing high soluble fiber, n-3 fatty acids and antioxidants as set forth reduce 4-EPS by increasing Parabacteroides, Blautia and Odoribacter and decreasing the genus in the family Pseudomonadaceae. Table 2 show the difference in the relative abundance of bacterial OTUs after the consumption of the prefeed, the control and the test foods.

In some embodiments based on the total weight of the composition on a dry matter basis, the amount of vitamin C is equal to 450 ppm, in some embodiments 475 ppm, in some embodiments 480 ppm, in some embodiments 485 ppm, in some embodiments 490 ppm, in some embodiments 500 ppm, in some embodiments 550 ppm or more and the amount of vitamin C is equal to 1000 IU/kg, in some embodiments 1200 IU/kg, in some embodiments 1300 IU/kg, in some embodiments 1400 IU/kg, in some embodiments 1500 IU/kg or more.

In some embodiments based on the total weight of the composition on a dry matter basis, the amount of insoluble fiber and soluble fiber equals 4.0%, in some embodiments 4.1%, 4.2%, in some embodiments 4.3%, in some embodiments 4.4%, in some embodiments 4.5%, in some embodiments 4.6%, in some embodiments 4.7%, 4.8%, in some embodiments 4.9% in some embodiments 5.0% or more, and the ratio of insoluble to soluble fiber (i.e. amount of insoluble fiber/amount of soluble fiber) is 2.0. 2.1, 2.2, 2.3, 2.4, 2.5, 2.6. 2.7, 2.8, 2.9, 3.0, and in some embodiments in the range of 2.4-2.6, and in some embodiments in the range of 2.4-2.5.

TABLE 2

| OTU | A | B | Difference (A − B) | Std Err Dif | p-Value |
| --- | --- | --- | --- | --- | --- |
| OTU1030652_g_Odoribacter | TEST | PF | 1.37 | 0.365 | 0.0007 |
| OTU1030652_g_Odoribacter | CTRL | PF | 1.14 | 0.365 | 0.006 |
| OTU1030652_g_Odoribacter | TEST | CTRL | 0.24 | 0.422 | 0.84 |
| OTU1000161_f_Pseudomonadaceae_unclassified | PF | CTRL | 1.97 | 0.417 | 1.38E−05 |
| OTU1000161_f_Pseudomonadaceae_unclassified | PF | TEST | 1.96 | 0.417 | 1.53E−05 |
| OTU1000161_f_Pseudomonadaceae_unclassified | TEST | CTRL | 0.01 | 0.48 | 0.9998 |
| OTU689975_g_Parabacteroides | TEST | PF | 1.23 | 0.23 | 6.28E−07 |
| OTU689975_g_Parabacteroides | CTRL | PF | 1.11 | 0.23 | 6.54E−06 |
| OTU689975_g_Parabacteroides | TEST | CTRL | 0.12 | 0.26 | 0.8973 |
| OTU361186_g_Blautia | TEST | PF | 1.3 | 0.33 | 0.00025 |
| OTU361186_g_Blautia | CTRL | PF | 1.25 | 0.33 | 0.0006 |
| OTU361186_g_Blautia | TEST | CTRL | 0.07 | 0.38 | 0.98 |

Example 2

The following composition is based upon total nutrition to be provided per day.

In some embodiments based on the total weight of the composition on a dry matter basis, the amount of n-3 fatty acids is equal to 0.6-0.9% of daily nutritional intake, the amount of vitamin C is equal to above 400 ppm of daily nutritional intake, the amount of vitamin E is equal to above 1000 IU/kg of daily nutritional intake, the amount of insoluble fiber and soluble fiber is equal to about 4.0-6.0% at a ratio (insoluble/soluble) in the range of between 2.0 and 3.0. In some embodiments, based on the total weight of the composition on a dry matter basis, the compositions comprise chicken in an amount from 5% to 25%, egg protein in an amount from 4% to 15%, corn gluten meal in an amount from 6% to 20%, vegetables thereof, in an amount from 0.5% to 2%, fruit in an amount from 0.5% to 2%, and a carbohydrate selected from millet, brewers rice, oat groats, and combinations thereof in an amount of 5% to 50% based on the total weight of the composition on a dry matter basis.

In some embodiments based on the total weight of the composition on a dry matter basis, the amount of n-3 fatty acid is in some embodiments 0.65-0.85%, of daily nutritional intake, in some embodiments 0.70-0.80% of daily nutritional intake, in some embodiments 0.72-0.79% of daily nutritional intake.

In certain embodiments, compositions may comprise chicken in an amount of 5%, 7.5%, 10%, 12.5%, 15%, 17.5%, 20%, 22.5% or 25% based on the total weight of the composition on a dry matter basis. In certain embodiments, compositions may comprise egg protein in an amount of 4%, 5%, 6%, 7%, 8%, 9%, 10%, 11%, 12%, 13%, 14% or 15% based on the total weight of the composition on a dry matter basis. In certain embodiments, compositions may comprise corn gluten meal in an amount of 6%, 7%, 8%, 9%, 10%, 11%, 12%, 13%, 14%, 15%, 16%, 17%, 18%, 19%, or 20% based on the total weight of the composition on a dry matter basis. In certain embodiments, compositions may comprise a vegetable source in an amount of 0.0%, 0.5%, 0.6%, 0.7%, 0.8%, 0.9%, 1.0%, 1.1%, 1.2%, 1.3%, 1.4%, 1.5%, 1.6%, 1.7%, 1.8%, or 1.9%, or 2.0% based on the total weight of the composition on a dry matter basis. In certain embodiments, compositions may comprise a fruit source in an amount of 0.0%, 0.5%, 0.6%, 0.7%, 0.8%, 0.9%, 1.0%, 1.1%, 1.2%, 1.3%, 1.4%, 1.5%, 1.6%, 1.7%, 1.8%, or 1.9%, or 2.0% based on the total weight of the composition on a dry matter basis. In certain embodiments, compositions may comprise a carbohydrate selected from millet, brewers rice, oat groats, and combinations thereof in an amount of 5%, 10%, 15%, 20%, 25%, 30%, 35%, 40%, 45%, or 50% based on the total weight of the composition on a dry matter basis. In particular aspects of these embodiments, composition of the invention may comprise a dry weight of a carbohydrate source within a range defined by any two of these values as endpoints.

Example 3

Table 3 describes certain embodiments having proportion of the composition (% of dry weight of component composition)

TABLE 3

| | |
|---|---|
| n-3 fatty acids | from about 0.60-0.90%, or |
| | from about 0.65-0.85%, or |
| | from about 0.70-0.80%, or |
| | from about 0.72-0.79%, or |
| Vitamin C | from 400 ppm or more, or |
| | from 450 ppm or more, or |
| | from 475 ppm or more, or |
| | from 480 ppm or more, or |
| | from 485 ppm or more, or |
| | from 490 ppm or more, or |
| | from 500 ppm or more, or |
| | from 550 ppm or more |
| Vitamin E | from 1000 IU/kg or more, or |
| | from 1100 IU/kg or more, or |
| | from 1200 IU/kg or more, or |
| | from 1300 IU/kg or more, or |
| | from 1400 IU/kg or more, or |
| | from 1500 IU/kg or more |
| Insoluble fiber and soluble fiber | from 4.0% or more, or |
| | from 4.5% or more, or |
| | from 4.6% or more, or |
| | from 4.7% or more, or |
| | from 4.8% or more, or |
| | from 4.9% or more, or |
| | from 5.0% or more |
| Ratio insoluble fiber/soluble fiber | from between 2.0 and 3.0, or |
| | from between 2.1 and 2.9, or |
| | from between 2.2 and 2.8, or |
| | from between 2.3 and 2.7, or |
| | from between 2.4 and 2.6, or |
| | from between 2.4 and 2.5 |
| Other Protein | from about 5% to about 70%, or |
| | from about 10% to about 70%, or |
| | from about 10% to about 60% |
| Carbohydrate (preferably a nitrogen-free or essentially nitrogen-free extract) | from about 0% to about 50%, or |
| | from about 5% to about 45% |
| Fat | from about 2% to about 50%, or |
| | from about 5% to about 50%, or |
| | from about 5% to about 40% |
| Dietary fiber | from about 0% to about 40%, or |
| | from about 1% to about 20%, or |
| | from about 1% to about 5.5% |
| Nutritional balancing agents (e.g., vitamins other than vitamin C, and minerals) | from about 0% to about 15%, or |
| | from about 2% to about 8% |

A daily diet that comprises effective amounts of n-3 fatty acids, vitamin C, vitamin E, insoluble fiber and soluble fiber may provide benefit to dogs identified as having stress. In some embodiments, the methods comprise identifying a dog as having or suspected of having stress, a stress disorder or displaying symptoms of stress or a stress disorder and feeding it a daily diet that comprises effective amounts of n-3 fatty acids, vitamin C, vitamin E, insoluble fiber and soluble fiber.

Example 4

Table 4 describes ingredients used in certain embodiments having proportion of the composition (% of dry matter weight of component composition).

TABLE 4

| Description | Content Range w/w % except as noted* |
|---|---|
| n-3 fatty acid | 0.6-0.9 |
| Vitamin C | 400 or more ppm* |
| Vitamin E | 1000 or more IU/kg* |
| Insoluble and soluble fiber | 4.0-5.0 |
| Ratio insoluble/soluble fiber | Ratio equals between 2.0 and 3.0* |
| Chicken, livers, hydrolyzed, dry | 25-45 |
| Hyvital ® wheat glutamine PN | 0.25-2 |
| Lysine, 1, hydrochloride | 0.1-0.75 |
| Methionine, dl | <0.08 |
| Taurine | 0.075-0.2 |
| Captex ® 355 Medium Chained Triglyceride | 1-5 |
| Cellulose, coarse | 1-5 |
| Beet, pulp | 1-3 |
| OatWell ® 22 oat bran | 2-5 |
| Pecan Fiber | 1-5 |
| MEG-3 ® 0355TG Fish Oil | 0.5-2.5 |
| Ginger Root Powder | 0.5-2 |
| Cranberry Pomace | 0.1-0.4 |
| Pomegranate Extract WS | 0.1-0.4 |
| Green Tea PE 50% EGCG WS | 0.1-0.4 |
| Boswellia PE 65% Boswellic Acids | 0.05-0.3 |
| Sensimune ™ 75 (Yeast Cell Wall) | 0.05-0.3 |

Example 5

Table 5 describes ingredients used in certain embodiments having proportion of the composition (% of dry matter weight of component composition).

TABLE 5

| Ingredient | w/w % except as noted* |
|---|---|
| n-3 fatty acid | 0.72-0.79 |
| Vitamin C | 400 ppm* |
| Vitamin E | 1000 IU/Kg |
| Insoluble and soluble fiber | 4.74-4.89 |
| Ratio insoluble/soluble fiber | 2.39-2.49 |
| Chicken, livers, hydrolyzed, dry | 32.79-36.79 |
| Corn, starch, common canning | 28.45-32.45 |
| Choice White Grease | 1.00 |
| Mineral, premix, 2305 | 0.08 |
| Vitamin E, oil, 29% | 0.10 |
| Hyvital ® Wheat Glutamine PN | 1.00 |
| Lysine, 1, hydrochloride | 0.50 |
| Methionine, dl | 0.07 |
| Taurine | 0.10 |
| Captex ® 355 Medium Chained Triglyceride | 4.00 |
| Cellulose, coarse | 3.00 |
| Lactic acid, food grade | 1.50 |
| Dicalcium phosphate | 1.20 |
| Chicken, liver, digest, optimizor LDPE H | 2.00 |
| Sodium chloride, iodized | 0.40 |
| Choline chloride, liquid, 70% | 0.25 |
| Calcium carbonate | 2.00 |
| Potassium chloride | 0.70 |
| Beet, pulp | 2.50 |
| OatWell ® 22 oat bran | 3.00 |
| Pecan Fiber | 2.00 |
| MEG-3 ® 0355TG Fish Oil | 1.50 |
| Ginger Root Powder | 1.00 |
| Palatant | 0.75 |
| Natural flavor, Pork, Liver, Digest, D'T | 0.50 |
| Glyceryl monostearate | 0.25 |
| Cranberry Pomace | 0.20 |
| Pomegranate Extract WS | 0.20 |
| Green Tea PE 50% EGCG WS | 0.20 |
| Boswellia PE 65% Boswellic Acids | 0.20 |
| Sensimune ™ 75 (Yeast Cell Wall) | 0.15 |

Example 6

Table 6 describes ingredients used in certain embodiments having proportion of the composition (% of dry matter weight of component composition).

TABLE 6

| Ingredient | w/w % except as noted* |
|---|---|
| n-3 fatty acid | 0.72-0.79 |
| Vitamin C | 400 ppm* |
| Vitamin E | 1000 IU/kg |
| Insoluble and soluble fiber | 4.74-4.89 |
| Ratio insoluble/soluble fiber | 2.39-2.49 |
| Rice, brewers | 23.00-25.00 |
| Pea, protein concentrate | 9.00-10.00 |
| Chicken Dried 10% Ash | 7.00-9.00 |
| Chicken, ground, fresh | 6.00-7.00 |
| Sorghum, whole | 6.36 |
| Chicken Meal | 6.14 |
| Pork Fat, Choice White Grease | 1.00 |
| Flax, seed, whole | 3.00 |
| Eggs, dried, granulated | 5.50 |
| Pecan Fiber | 4.80 |
| G03 Buckwheat Groats | 4.00 |
| Oat, groats | 4.00 |
| Captex 355 Medium Chained Triglyceride | 3.00 |
| Chicken, liver, digest, optimizor LDPE H | 2.00 |
| Oat, fiber | 1.50 |
| Beet, pulp, ground, fine | 1.50 |
| Lactic acid, food grade | 1.50 |
| Fish oil, TG, 18/12, NP | 1.20 |
| Flav Gen#1 + CWG | 1.00 |
| Potassium chloride | 0.30 |
| Carnitine, 1, 10% | 0.27 |
| Natural flavor, Pork, Liver, Digest, D'T | 0.25 |
| Choline chloride, liquid, 70% | 0.18 |
| Sensimune 75 (Yeast Cell Wall) | 0.15 |
| Vitamin E, oil, 29% | 0.14 |
| Taurine | 0.10 |
| Sodium chloride, iodized | 0.10 |
| Lysine, 1, hydrochloride | 0.10 |
| Mineral, premix, 2305 | 0.04 |
| Oat Fiber, Fruit, Vegetable blend | 0.04 |
| Dicalcium phosphate | 0.04 |

Example 7

Table 7 describes ingredients used in certain embodiments having proportion of the composition (% of dry matter weight of component composition).

TABLE 7

| Ingredient | w/w % except as noted* |
|---|---|
| n-3 fatty acid | 0.72-0.79 |
| Vitamin C | 400 ppm* |
| Vitamin E | 1000 IU/kg |
| Insoluble and soluble fiber | 4.74-4.89 |
| Ration insoluble/soluble fiber | 2.39-2.49 |
| Rice, Brewers | — |
| Chicken Meal | 6.00-7.00 |
| Pea, protein concentrate | 7.00-8.00 |
| Cellulose, coarse | 3.00-4.00 |
| Chicken Dried 10% Ash | 5.00-6.00 |
| Barley, pearled, cracked | 18.00-20.00 |
| Chicken, ground, fresh | 7.00-8.00 |
| Flax, seed, whole | 2.00 |
| Coconut oil preserved | 4.00 |
| Chicken, liver, digest, optimizer LDPE H | 3.00 |
| Lactic acid | 1.50 |
| Methionine, dl | 0.64 |
| Potassium chloride | 0.50 |
| Sodium chloride, iodized | 0.60 |
| Fish oil, TG, 18/12, NP | 0.50 |
| Calcium carbonate | 0.30 |
| Choline chloride, liquid, 70% | 0.25 |
| Carnitine, 1, 10% | 0.30 |
| Vitamin E, oil, 29% | 0.17 |
| Mineral, premix, 2305 | 0.08 |
| Taurine | 0.06 |
| Oat, groats | 10.00 |
| Buckwheat Groats | 6.92 |
| Pea, bran, meal | 5.00 |
| Tomato, pomace, | 5.00 |
| Beet, pulp, ground, fine | 3.00 |

Example 8

Table 8 describes ingredients used in certain embodiments having proportion of the composition (% of dry matter weight of component composition).

TABLE 8

| Ingredient | w/w % except as noted* | w/w % except as noted* |
|---|---|---|
| n-3 fatty acid | 0.6-0.9 | 0.6-0.9 |
| Vitamin C | 400 or more ppm* | 400 or more ppm* |
| Vitamin E | 1000 or more IU/kg* | 1000 or more IU/kg* |
| Insoluble and soluble fiber | 4.0-5.0 | 4.0-5.0 |
| Ratio insoluble/soluble fiber | Ratio between 2.0 and 3.0* | Ratio between 2.0 and 3.0* |
| Corn starch | 31.10 | 48.11 |
| Hydrolyzed chicken liver and heart | 37.00 | 32.00 |
| Soybean oil, crude, degummed | 3.60 | 4.66 |
| Cellulose, pelleted | — | 3.94 |
| Chicken, liver, digest, optimizer LDPE H | 2.00 | 2.00 |
| Lactic acid, food grade | 1.50 | 1.50 |
| Calcium carbonate | 1.22 | 1.22 |
| Dicalcium phosphate | 1.22 | 1.22 |
| Choice White Grease/Phos Acid | 1.25 | 1.00 |
| Flav Gen#1 + CWG | 1.25 | 0.75 |
| Glyceryl monostearate | 0.74 | 0.74 |
| Potassium chloride | 0.69 | 0.69 |
| Natural flavor, Pork, Liver, Digest, D'T | 0.75 | 0.50 |
| Sodium chloride, iodized | 0.44 | 0.44 |
| Choline chloride, liquid, 70% | 0.38 | 0.38 |
| Methionine, dl | 0.30 | 0.30 |
| Sodium tripolyphosphate | 0.15 | 0.15 |
| Vitamin premix | 0.12 | 0.12 |
| Mineral, premix, 2305 | 0.07 | 0.07 |
| Taurine | 0.02 | 0.02 |
| Pecan shells, ground | 7.00 | — |
| Flax seed whole brown | 3.00 | — |
| Beet pulp, ground, fine | 2.50 | — |
| Cranberry pomace | 1.00 | — |

Example 9

Table 9 describes ingredients used in certain embodiments having proportion of the composition (% of dry matter weight of component composition).

TABLE 9

| Ingredient | w/w % except as noted* | w/w % except as noted* |
| --- | --- | --- |
| n-3 fatty acid | 0.6-0.9 | 0.6-0.9 |
| Vitamin C | 400 or more ppm* | 400 or more ppm* |
| Vitamin E | 1000 or more IU/kg* | 1000 or more IU/kg* |
| Insoluble and soluble fiber | 4.0-5.0 | 4.0-5.0 |
| Ratio insoluble/soluble fiber | Ratio between 2.0 and 3.0* | Ratio between 2.0 and 3.0* |
| Chicken meal | 15.36 | 15.36 |
| Rice, brewers | 8.64 | 8.64 |
| Eggs, dried, granulated | 8.00 | 8.00 |
| Corn, gluten, meal | 7.62 | 7.62 |
| Sorghum, whole | 5.00 | 5.00 |
| Choice white grease/Phos Acid | 4.00 | 4.00 |
| Palatant, 12 L, Liquid | 3.00 | 3.00 |
| Lactic acid, food grade | 1.50 | 1.50 |
| Soybean oil, crude, degummed | 1.05 | 1.05 |
| Palatant, ITE2, Dry | 1.00 | 1.00 |
| Potassium chloride | 0.89 | 0.89 |
| Sodium chloride, iodized | 0.61 | 0.61 |
| Calcium carbonate | 0.41 | 0.41 |
| Dicalcium phosphate | 0.25 | 0.25 |
| Vitamin E, oil, 29% | 0.17 | 0.17 |
| Choline chloride, liquid, 70% | 0.16 | 0.16 |
| Mineral, premix, 2305 | 0.06 | 0.06 |
| Tryptophan | 0.04 | 0.04 |
| Taurine | 0.04 | 0.04 |
| Cellulose, pelleted | — | 1.50 |
| Corn, yellow, whole | 26.00 | 40.00 |
| Pecan shells, ground | 7.00 | — |
| Flax seed whole brown | 3.00 | — |
| Beet pulp, ground, fine | 2.50 | 0.50 |
| Cranberry pomace | 1.00 | — |

Example 10

Table 10 describes ingredients used in certain embodiments having proportion of the composition (% of dry matter weight of component composition).

TABLE 10

| Ingredient | w/w %* | w/w %* | w/w %* | w/w %* | w/w %* |
| --- | --- | --- | --- | --- | --- |
| n-3 fatty acids | 0.6-0.9 | 0.6-0.9 | 0.6-0.9 | 0.6-0.9 | 0.6-0.9 |
| Vitamin C | 400 or more ppm* | 400 or more ppm* | 400 or more ppm* | 400 or more ppm* | 400 or more ppm* |
| Vitamin E | 1000 or more IU/kg* | 1000 or more IU/kg* | 1000 or more IU/kg* | 1000 or more IU/kg* | 1000 or more IU/kg* |
| Insoluble and soluble fiber | 4.0-5.0 | 4.0-5.0 | 4.0-5.0 | 4.0-5.0 | 4.0-5.0 |
| Ratio Insoluble/soluble fiber | Ratio equals between 2.0 and 3.0* | Ratio equals between 2.0 and 3.0* | Ratio equals between 2.0 and 3.0* | Ratio equals between 2.0 and 3.0* | Ratio equals between 2.0 and 3.0* |
| Vitamin C | 0.012-0.034 | 0.012-0.034 | 0.012-0.034 | 0.012-0.034 | 0.012-0.034 |
| Coconut Oil | 14.2 | 7.1 | 14.2 | 13.0 | 13.0 |
| Protein | 19.7 | 24.7 | 24.7 | 24.8 | 24.8 |
| Fat | 20.6 | 16.9 | 16.9 | 22.0 | 22.0 |
| Carbohydrate | 53.8 | 51.0 | 51.0 | 46.3 | 27.6 |
| Crude Fiber | 0.37 | 2.6 | 2.6 | 1.4 | 21.0 |

*except as noted

The invention claimed is:

1. A method for reducing levels of 4-ethylphenyl sulfate in an animal comprising:
    administering to the animal in need thereof an effective amount of a food composition comprising: n-3 fatty acids, antioxidants, Vitamin C, Vitamin E, insoluble fiber, and soluble fiber,
    wherein the insoluble fiber and the soluble fiber are present in a ratio of from 2.0 to 3.0,
    wherein the Vitamin C is present in an amount greater than 400 ppm,
    wherein the Vitamin E is present in an amount greater than 1000 IU/kg,
    wherein the n-3 fatty acids are present in an amount of from 0.6% to 0.9%,
    wherein the administering of the food composition treats anxiety or stress in the animal.

2. The method of claim 1 wherein the animal is administered n-3 fatty acids equal to 0.65-0.85% of nutritional intake per day.

3. The method of claim 1 wherein the animal is administered n-3 fatty acids equal to 0.70-0.75% of nutritional intake per day.

4. The method of claim 1 wherein the animal is administered n-3 fatty acids equal to 0.72-0.79% of nutritional intake per day.

5. The method of claim 1 wherein the animal is administered Vitamin C equal to 450 ppm of nutritional intake per day.

6. The method of claim 1 wherein the animal is administered Vitamin C equal to 475 ppm of nutritional intake per day.

7. The method of claim 1 wherein the animal is administered Vitamin C equal to 490 ppm of nutritional intake per day.

8. The method of claim 1 wherein the animal is administered Vitamin E equal to 1100 IU/kg of nutritional intake per day.

9. The method of claim 1 wherein the animal is administered Vitamin E equal to 1200 IU/kg of nutritional intake per day.

10. The method of claim 1 wherein the animal is administered Vitamin E equal to 1400 IU/kg of nutritional intake per day.

11. The method of claim 1, wherein the ratio of the insoluble fiber to the soluble fiber is from 2.2 to 2.7.

12. The method of claim 1, wherein the ratio of the insoluble fiber to the soluble fiber is from 2.3 to 2.6.

13. The method of claim 1, wherein the ratio of the insoluble fiber to the soluble fiber is from 2.4 to 2.5.

14. The method of claim 1 wherein the animal is administered insoluble fiber and soluble fiber an amount equal to 4.0-5.5% of nutritional intake per day.

15. The method of claim 1 wherein the animal is administered insoluble fiber and soluble fiber an amount equal to 4.5-5.0% of nutritional intake per day.

16. The method of claim 1 wherein the animal is administered insoluble fiber and soluble fiber an amount equal to 4.7-4.9% of nutritional intake per day.

17. The method of claim 1 wherein the animal is a canine.

18. The method of claim 17 wherein the canine is identified as having an elevated level of 4-ethylphenyl sulfate.

19. The method of claim 17 wherein the canine has previously been identified as having canine anxiety.

20. The method of claim 17 wherein the canine has previously been identified as having canine stress symptoms.

21. A food composition comprising an effective amount of n-3 fatty acids, vitamin C, vitamin E, insoluble fiber and soluble fiber to treat anxiety, stress or a stress disorder in an animal, wherein the effective amount of n-3 fatty acids equal to 0.6-0.9% of nutritional intake per day, vitamin C at a level of 400 ppm or more of nutritional intake per day, vitamin E at a level of 1000 IUK of nutritional intake per day and insoluble fiber and soluble fiber in a ratio of insoluble fiber/soluble fiber of between 2.0 and 3.0.

22. The food composition of claim 21, wherein the effective amount of n-3 fatty acids equal to 0.65-0.85% of nutritional intake per day, vitamin C at a level of 450 ppm or more of nutritional intake per day, vitamin E at a level of 1100 IUK of nutritional intake per day and insoluble fiber and soluble fiber in a ratio of insoluble fiber/soluble fiber of between 2.2 and 2.8.

23. The food composition of claim 21, wherein the effective amount of n-3 fatty acids equal to 0.70-0.80% of nutritional intake per day, vitamin C at a level of 475 ppm or more of nutritional intake per day, vitamin E at a level of 1200 IUK of nutritional intake per day and insoluble fiber and soluble fiber in a ratio of insoluble fiber/soluble fiber of between 2.3 and 2.7.

24. The food composition of claim 21, wherein the effective amount of n-3 fatty acids equal to 0.72-0.79% of nutritional intake per day, vitamin C at a level of 490 ppm or more of nutritional intake per day, vitamin E at a level of 1400 IUK of nutritional intake per day and insoluble fiber and soluble fiber in a ratio of insoluble fiber/soluble fiber of between 2.4 and 2.5.

25. The food composition of claim 21 wherein the amount of insoluble fiber and soluble fiber is equal to 4.0-5.5% of nutritional intake per day.

26. The food composition of claim 21 wherein the amount of insoluble fiber and soluble fiber is equal to 4.5-5.0% of nutritional intake per day.

27. The food composition of claim 21 wherein the amount of insoluble fiber and soluble fiber is equal to 4.7-4.9% of nutritional intake per day.

28. The food composition of claim 21, wherein the food composition is a canine food composition.

29. The method of claim 1, further comprising identifying the animal in need thereof as having an elevated level of 4-ethylphenyl sulfate, wherein the animal in need thereof is a canine.

* * * * *